US008236561B2

(12) United States Patent
Jones et al.

(10) Patent No.: US 8,236,561 B2
(45) Date of Patent: *Aug. 7, 2012

(54) EFFICIENT PRODUCTION OF IGA IN RECOMBINANT MAMMALIAN CELLS

(75) Inventors: David H. A. Jones, London (GB); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 1640 days.

This patent is subject to a terminal disclaimer.

(21) Appl. No.: 10/644,256

(22) Filed: Aug. 20, 2003

(65) Prior Publication Data

US 2005/0106722 A1     May 19, 2005

Related U.S. Application Data

(63) Continuation-in-part of application No. 09/549,463, filed on Apr. 14, 2000, now Pat. No. 6,855,544, which is a continuation-in-part of application No. PCT/EP03/07690, filed on Jul. 15, 2003, application No. 10/644,256, which is a continuation-in-part of application No. PCT/EP03/50201, filed on May 27, 2003.

(60) Provisional application No. 60/129,452, filed on Apr. 15, 1999, provisional application No. 60/397,066, filed on Jul. 18, 2002.

(30) Foreign Application Priority Data

Jul. 18, 2002  (EP) ..................... 02077953

(51) Int. Cl.
   *C12N 5/071* (2010.01)
   *C12N 15/85* (2006.01)
(52) U.S. Cl. ....................... 435/366; 435/325
(58) Field of Classification Search .............. None
   See application file for complete search history.

(56) References Cited

U.S. PATENT DOCUMENTS

| | | | |
|---|---|---|---|
| 4,703,008 A | 10/1987 | Lin | |
| 4,835,260 A | 5/1989 | Shoemaker | |
| 5,047,335 A | 9/1991 | Paulson et al. | |
| 5,192,539 A | 3/1993 | Van Der Marel et al. | |
| 5,441,868 A | 8/1995 | Lin | |
| 5,457,089 A | 10/1995 | Fibi et al. | |
| 5,494,790 A | 2/1996 | Sasaki et al. | |
| 5,631,158 A | 5/1997 | Dorai et al. | |
| 5,767,078 A | 6/1998 | Johnson et al. | |
| 5,773,569 A | 6/1998 | Wrighton et al. | |
| 5,789,247 A | 8/1998 | Ballay et al. | |
| 5,830,851 A | 11/1998 | Wrighton et al. | |
| 5,835,382 A | 11/1998 | Wilson et al. | |
| 5,856,298 A | 1/1999 | Strickland | |
| 5,994,128 A | 11/1999 | Fallaux et al. | |
| 6,033,908 A | 3/2000 | Bout et al. | |
| 6,475,753 B1* | 11/2002 | Ruben et al. ................. | 435/69.1 |
| 6,492,169 B1 | 12/2002 | Vogels et al. | |
| 6,558,948 B1 | 5/2003 | Kochanek et al. | |
| 6,653,101 B1 | 11/2003 | Cockett et al. | |
| 6,821,512 B1* | 11/2004 | Gao et al. ..................... | 424/93.2 |
| 6,855,544 B1 | 2/2005 | Hateboer et al. | |
| 6,878,549 B1 | 4/2005 | Vogels et al. | |
| 2002/0116723 A1 | 8/2002 | Grigliatti et al. | |
| 2003/0087437 A1 | 5/2003 | Asada et al. | |
| 2003/0092160 A1 | 5/2003 | Bout et al. | |
| 2005/0170398 A1* | 8/2005 | Van Berkel et al. ............... | 435/6 |
| 2005/0221492 A1 | 10/2005 | Fallaux et al. | |
| 2008/0171018 A1 | 7/2008 | Bout et al. | |
| 2009/0023196 A1 | 1/2009 | Fallaux et al. | |
| 2009/0170164 A1 | 7/2009 | Hateboer et al. | |
| 2009/0253207 A1 | 10/2009 | Vogels et al. | |

FOREIGN PATENT DOCUMENTS

| | | |
|---|---|---|
| EP | 0 185 573 | 6/1986 |
| EP | 0 411 678 | 2/1991 |
| EP | 0 833 934 B1 | 4/1998 |
| WO | WO 93/03163 | 2/1993 |
| WO | WO 95/05465 | 2/1995 |
| WO | WO 95/29994 | 11/1995 |
| WO | WO/97/00326 * | 1/1997 |
| WO | WO 97/00326 | 1/1997 |
| WO | WO 98/18926 | 5/1998 |
| WO | WO 98/39411 | 9/1998 |
| WO | WO 98/44141 | 10/1998 |
| WO | WO 99/05268 | 2/1999 |
| WO | WO 99/24068 | 5/1999 |
| WO | WO 00/61164 | 10/2000 |
| WO | WO 00/63403 | 10/2000 |
| WO | WO 01/38362 A2 | 5/2001 |
| WO | WO 02/053580 | 7/2002 |
| WO | WO 03/038100 A1 | 5/2003 |
| WO | WO 03/048197 A1 | 6/2003 |
| WO | WO 03/048348 A2 | 6/2003 |

(Continued)

OTHER PUBLICATIONS

Ory, et al. A Stable Human-Derived Packaging Cell Line for Production of High Titer Retroviru/Vesicular Stomatitus virus G Pseudotypes, Proc. Natl. Acad. Sci. 93:11400-11406, 1996.*

Caravokyri, et al. Constitutive Episomal Expression of Polypeptide IX (pIX) in a 293-Based Cell Line Complements that Deficiency of pIX Mutant Adenovirus Type 5, Journal of Virology 69(11):6627-6633, 1995.*

Yallop et al., "PER.C6® Cells for the Manufacture of Biopharmaceutical Proteins," Modern Biopharmaceuticals, Ed. J. Knablein, 2005, Wiley-VCH Verlag GmbH & Co. KGaA, Weinheim, Germany.

U.S. Appl. No. 12/932,719, filed Mar. 4, 2011, Van Berkel et al., Recombinant Production of Mixtures of Antibodies.

(Continued)

*Primary Examiner* — Michele K Joike (74) *Attorney, Agent, or Firm* — TraskBritt (57) ABSTRACT

The invention provides an immortalized human retina cell expressing E1A and E1B proteins of an adenovirus, wherein the cell has recombinant nucleic acid encoding an IgA molecule in expressible format. Also provided is a method for recombinant production of an IgA molecule, the method involving culturing a cell of the invention and expressing the recombinant nucleic acid encoding an IgA.

1 Claim, 2 Drawing Sheets

FOREIGN PATENT DOCUMENTS

| WO | WO 03/051927 | 6/2003 |
|----|----|----|
| WO | WO 2004/003176 | 1/2004 |
| WO | WO 2004/099396 | 11/2004 |

OTHER PUBLICATIONS

Alkhatib et al., "Expression of Bicistronic Measles Virus P/C mRNA by Using Hybrid Adenovirus: Levels of C Protein Synthesized In Vivo Are Unaffected by the Presence or Absence of the Upstream P Initiator Codon," Journal of Virology, Nov. 1988, pp. 4059-4068, vol. 62, No. 11.

Alkhatib et al., "High-Level Eurcaryotic In Vivo Expression of Biologically Active Measles Virus Hemagglutinin by Using an Adenovirus Type 5 Helper-Free Vector System," Journal of Virology, Aug. 1988, pp. 2718-2727, vol. 62, No. 8.

Berg et al., High-Level Expression of Secreted Proteins from Cells Adapted to Serum-Free Suspension Culture, Research Report, BioTechniques, 1993, pp. 972-978, vol. 14, No. 6.

Brown et al., "Evaluation of Cell Line 293 for Virus isolation in Routine Viral Diagnosis," Journal of Clinical Microbiology, Apr. 1986, pp. 704-708, vol. 23, No. 4.

Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.

Caravokyri et al., "Constitutive Episomal Expression of Polypeptide IX (pIX) in a 293-Based Cell Line Complements that Deficiency of pIX Mutant Adenovirus Type 5," Journal of Virology, Nov. 1995, pp. 6627-6633, vol. 69, No. 11.

Certificate of deposit of the PER.C6 cell line (ECACC deposit under No. 96022940), 2004.

Ciccarone et al., "Lipofectamine 2000 Reagent for Transfection of Eukaryotic Cells," Focus, 1999, pp. 54-55, vol. 21, No. 2.

Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.

DuBridge et al., "Analysis of Mutation in Human Cells by Using an Epstein-Barr Virus Shuttle System," Molecular and Cellular Biology, Jan. 1987, pp. 397-387, vol. 7, No. 1.

Endo et al., Growth of Influenza A Virus in Primary, Differentiated Epithelial Cells Derived from Adenoids, Journal of Virology, Mar. 1996, pp. 2055-2058, vol. 70, No. 3.

Fallaux et al., Characterization of 911: A New Helper Cell Line for the Titration and Propagation of Early Region 1-Deleted Adenoviral Vectors, Human Gene Therapy, Jan. 20, 1996, pp. 215-222, vol. 7.

Figure 1 submitted by Opponent I, submitted 2006.

Gallimore et al., Transformation of Human Embryo Retinoblasts with Simian Virus 40, Adenovirus and ras Oncogenes, Anticancer Research, 1986, pp. 499-508, vol. 6.

Garnier et al., Scale-up of the adenovirus expression system for the production of recombinant protein in human 293S cells, Cytotechnology, 1994, pp. 145-155, vol. 15.

GenBank Accession No. X02996.1, 1993, "Adenovirus type 5 left 32% of the genome."

GIBCO cell culture, A Guide to Serum-Free Cell Culture, www.invitrogen.com, 2003.

Graham et al., "Characteristics of a Human Cell Line Transformed by DNA from Human Adenovirus Type 5," J. Gen. Virol., 1997, pp. 59-72, vol. 36.

Graham et al., "Growth of 293 cells in suspension culture," J Gen Virol, Mar. 1987, pp. 937-940, vol. 68.

Graham, Cell Lines, Promochem (visited Apr. 10, 2005) <http://www.lgcpromochem-atcc.com/SearchCatalogs/longview.cfm?view=ce,1146678...>.

Holzer et al., "Construction of a Vaccinia Virus Deficient in the Essential DNA Repair Enzyme Uracil DNA Glycosylase by a Complementing Cell Line," Journal of Virology, Jul. 1997, pp. 4997-5002, vol. 71, No. 7.

Inoue et al., Production of Recombinant Human Monoclonal Antibody Using ras-Amplified BHK-21 Cells in a Protein-free Medium, Biosci. Biotech. Biochem., 1996, pp. 811-817, vol. 60, No. 5.

Interlocutory Decision of the Opposition Division of Jul. 21, 2003 in the case EP 0 695 351(European application 94 913 174.2).

Lopez et al., Efficient production of biologically active human recombinant proteins in human lymphoblastoid cells form integrative and episomal expression vectors, Gene, 1994, pp. 285-291, vol. 148.

Lutz et al., "The Product of the Adenovirus Intermediate Gene IX Is a Transcriptional Activator," Journal of Virology, Jul. 1997, pp. 5102-5109, vol. 71, No. 7.

Manservigi et al., "Protection from Herpes Simplex Virus Type I Lethal and Latent Infections by Secreted Recombinant Glycoprotein B Constitutively Expressed in Human Cells with a BK Virus Episomal Vector," Journal of Virology, Jan. 1990, pp. 431-436, vol. 64, No. 1.

Marketing Authorization and Scientific Discussion for Xigris, 2002.

Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.

Merten et al., Production of Influenza Virus in Cell Cultures for Vaccine Preparation, Exp Med Biol., 1996, pp. 141-151, vol. 397.

Neumann et al., "Generation of influenza A viruses entirely from cloned cDNAs," Proc. Natl. Acad. Sci., Aug. 1999, pp. 9345-9350, vol. 96.

Notice of Opposition to a European Patent for 1 161 548 by Serono, 2005.

Opposition against European patent 1 108 878 B1 filed Oct. 5, 2005 in the name and on behalf of CEVEC Pharmaceuticals GmbH.

Opposition against European patent 1 161 548 B1 filed Nov. 16, 2005, in the name and on behalf of CEVEC Pharmaceutical GmbH.

Opposition against European patent 1108787 filed Oct. 5, 2005 in the name and on behalf of Probiogen AG.

Ory et al., "A stable human-derived packaging cell line for production of high titer retrovirus/vesicular stomatitis virus G pseudotypes," Proc. Natl. Acad. Sci., Oct. 1996, pp. 11400-11406, vol. 93.

Parkinson et al., "Stable Expression of a Secretable Deletion Mutant of Recombinant Human Thrombomodulin in Mammalian Cells," The Journal of Biological Chemistry, Jul. 25, 1990, pp. 12602-12610, vol. 265, No. 21.

Paul et al., Increased Viral Titer Through Concentration of Viral Harvests from Retroviral Packaging Lines, Human Gene Therapy, 1993, pp. 609-615, vol. 4.

Pleschka et al., "A Plasmid-Based Reverse Genetics System for Influenza A Virus," Journal of Virology, Jun. 1996, pp. 4188-4192, vol. 70, No. 6.

PubMed listing of abstracts (visited Apr. 10, 2005) <http://www.ncbi.nlm.nih.gov/entrez/query.fcgi?CMD=search&DB=pubmed.

Reina et al., Comparison of Madin-Darby Canine Kidney cells (MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Rhim et al., "Development of Human Cell Lines from Multiple Organs," Annals of the New York Academy of Sciences, 2000, pp. 16-25, vol. 919.

Spector et al., "Regulation of Integrated Adenovirus Sequences During Adenovirus Infection of Transformed Cells," Journal of Virology, Dec. 1980, pp. 860-871, vol. 36, No. 3.

Stevens et al., "The N-Terminal Extension of the Influenza B Virus Nucleoprotein Is Not Required for Nuclear Accumulation or the Expression and Replication of a Model RNA," Journal of Virology, Jun. 1998, pp. 5307-5312, vol. 72, No. 6.

U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1999 (visited Sep. 30, 2005) <http://www.fda.gov.cber.minutes/0910evolv.txt>.

Yan et al., Novel Asn-linked oligosaccharides terminating in GalNAcbeta(1-4)[Fucalpha(1-3)]GlcNAcbeta(1-.) are present in recombinant human Protein C expressed in human kidney 293 cells, Glycobiology, 1993, pp. 597-608, vol. 3. No. 6.

Yeager et al., Constructing immortalized human cell lines, Current Opinion Biotechnology, 1999, pp. 465-469, vol. 10.
Yeh et al., Adenoviral Vectors, pp. 25-42 of "Concepts in Gene Therapy," Publisher: Walter de Gruyter, New York, 2006, submitted.
Ghosh-Choudhury et al., Protein IX, a minor component of the human adenovirus capsid, is essential for the packaging of the full length genomes, The EMBO Journal, 1987, pp. 1733-1739, vol. 6, No. 6.
Louis et al., Cloning and Sequencing of the Cellular-Viral Junctions from the Human Adenovirus Type 5 Transformed 293 Cell Line, Virology, 1997, pp. 423-429, vol. 233.
NCBI Entrez Nucleotide accession No. U38242, 2003.
NCBI Entrez Nucleotide accession No. NC_002018, 2003.
NCBI Entrez Nucleotide accession No. X02996 J01967 J01968 J01970 J01971 J01972 J01974 J01976 J01977 J01978 J01979 K00515 V00025 V00026 V00027 V00029, 2003.
Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-2953, vol. 84, No. 9.
U.S. Appl. No. 09/214,836, filed Oct. 4, 1999, Melanoma Associated Peptide Analogues and Vaccines Against Melanoma.
U.S. Appl. No. 09/332,803, filed Jun. 14, 1999, Packaging Systems for Human Recombinant Adenovirus to Be Used in Gene Therapy.
U.S. Appl. No. 09/348,354, filed Jul. 7, 1999, Chimaeric Adenoviruses.
U.S. Appl. No. 09/444,284, filed Nov. 19, 1999, Gene Delivery Vectors Provided With a Tissue Tropism for Smooth Muscle Cells, and/or Endothelial Cells.
U.S. Appl. No. 09/549,463, filed Apr. 14, 2000, Recombinant Protein Production in a Human Cell.
U.S. Appl. No. 09/517,898, filed Mar. 3, 2000, Means and Methods for Fibroblast-Like or Macrophage-Like Cell Transduction.
U.S. Appl. No. 09/573,740, filed May 18, 2000, Serotypes of Adenovirus and Uses Thereof.
U.S. Appl. No. 09/665,472, filed Sep. 20, 2000, Gene Delivey Vectors Provided With a Tissue Tropism for Dendritic Cells.
U.S. Appl. No. 09/843,894, filed Apr. 27, 2001, AAV Vector Production.
U.S. Appl. No. 09/900,062, filed Jul. 6, 2001, Packaging Systems for Human Recombinant Adenovirus to be Used in Gene Therapy.
U.S. Appl. No. 09/912,552, filed Jul. 23, 2001, Packaging Systems for Human Recombinant Adenovirus to Be Used in Gene Therapy.
U.S. Appl. No. 09/918,029, filed Jul. 30, 2001, Packaging Systems for Human Recombinant Adenovirus to Be Used in Gene Therapy.
U.S. Appl. No. 09/928,262, filed Aug. 10, 2001, Gene Delivery Vectors With Cell Type Specificity for Primary Human Chondrocytes.
U.S. Appl. No. 09/953,280, filed Sep. 14, 2001, Chimaeric Adenoviruses.
U.S. Appl. No. 10/010,645, filed Nov. 13, 2001, Gene Delivery Vectors With Cell Type Specificity for Mesenchymal Stem Cells.
U.S. Appl. No. 10/038,271, filed Oct. 23, 2001, Packaging Systems for Human Recombinant Adenovirus to Be Used in Gene Therapy.
U.S. Appl. No. 10/125,751, filed Apr. 18, 2002, Packaging Systems for Human Recombinant Adenovirus to Be Used in Gene Therapy.
U.S. Appl. No. 10/136,139, filed May 1, 2002, Means and Methods for Nucleic Acid Delivery Vehicle Design and Nucleic Acid Transfer.
U.S. Appl. No. 10/219,414, filed Aug. 15, 2002, Stocks of Replication Deficient Adenovirus.
U.S. Appl. No. 10/231,735, filed Aug. 28, 2002, Interleukin-3 Gene Therapy for Cancer.
U.S. Appl. No. 10/234,007, filed Sep. 3, 2002, Recombinant Protein Production in a Human Cell.
U.S. Appl. No. 10/305,435, filed Nov. 25, 2002, Methods and Means for Enhancing Skin Transplantation Using Gene Delivery Vehicles Having Tropism for Primary Fibroblasts, as Well as Other Uses thereof (Primaire Fibroblasten).
U.S. Appl. No. 10/381,088, filed Mar. 20, 2003, Adenoviral Vectors Provided With a Tropism for Dendritic Cells.
U.S. Appl. No. 10/381,857, filed Mar. 26, 2003, Adenoviral Vectors for Gene Delivery in Skeletal Muscle Cells or Myoblasts.
U.S. Appl. No. 10/396,548, filed Mar. 25, 2003, Packaging Systems for Human Recombinant Adenovirus to Be Used in Gene Therapy.
U.S. Appl. No. 10/618,526, filed Jul. 11, 2003, Packing Systems for Human Recombinant Adenovirus to Be Used in Gene Therapy.
PCT International Search Report, PCT/NL00/00247, dated Oct. 9, 2000, 3 pages.
U.S. Appl. No. 10/499,298, filed Oct. 25, 2004, Efficient Production of F(AB')2 Fragments in Mammalian Cells.
U.S. Appl. No. 10/512,589, filed Oct. 25, 2004, Means and Methods for the Production of Adenovirus Vectors.
U.S. Appl. No. 10/783,510, filed Feb. 20, 2004, Means and Methods for Fibroblast-Like or Macrophage-Like Cell Transduction.
U.S. Appl. No. 10/790,562, filed Mar. 1, 2004, Recombinant Protein Production in a Human Cell.
U.S. Appl. No. 10/808,681, filed Mar. 25, 2004, Melanoma Associated Peptide Analogues and Vaccines Against Melanoma.
U.S. Appl. No. 10/850,140, filed May 20, 2004, Packaging Systems for Human Recombinant Adenovirus to Be Used in Gene Therapy.
U.S. Appl. No. 10/951,102, filed Sep. 27, 2004, Serotypes of Adenovirus and Uses Thereof.
U.S. Appl. No. 11/018,669, filed Dec. 20, 2004, Gene Delivery Vectors Provided With a Tissue Tropism for Smooth Muscle Cells, and/or Endothelial Cells.
U.S. Appl. No. 11/039,767, filed Jan. 18, 2005, Recombinant Production of Mixtures of Antibodies.
U.S. Appl. No. 11/070,890, filed Mar. 2, 2005, Recombinant Protein Production in Permanent Amniocytic Cells That Comprise Nucleic Acid Encoding Adenovirus E1A and E1B Proteins.
U.S. Appl. No. 11/083,590, filed Mar. 18, 2005, Gene Delivery Vectors With Cell Type Specificity for Mesenchymal Stem Cells.
U.S. Appl. No. 11/134,674, filed May 19, 2005, Means and Methods for Nucleic Acid Delivery Vehicle Design and Nucleic Acid Transfer.
Bout et al., "Improved helper cells for RCA-free production of E1-deleted recombinant adenovirus vectors," Cancer Gene Therapy, 1996, pp. S24, vol. 3, No. 6.
Bout et al., "Production of RCA-free batches of E1-deleted recombinant adenoviral vectors on PER.C6," Nucleic Acids Symp. Ser. 1998, XP-002115716, pp. 35-36.
Boutl et al., A novel packaging cell line (PER.C6) for efficient production of RCA-free batches of E1-deleted recombinant adenoviral vectors, Cancer Gene Therapy, 1997, pp. S32-S33, vol. 4, No. 6.
Carroll et al., Abstract, Differential Infection of Receptor-modified Host Cells by Receptor-Specific Influenza Viruses, Virus Research, Sep. 1985, pp. 165-179, vol. 3, No. 2.
Cronan, Abstract, Biotination of Proteins in-vivo a post-translational modification to label purify and study proteins, Journal of Biological Chemistry, Jun. 25, 1990, pp. 10327-10333, vol. 265, No. 18.
European Search Report 05 10 0732, Apr. 7, 2005.
Fallaux et al, "New helper cells and matched early region 1-deleted adenovirus vectors prevent generation of replication-competent adenoviruses," Human Gene Therapy, Sep. 1, 1998, vol. 9, No. 1, pp. 1909-1917. Abstract.
Grabenhorst et al., Construction of stable BHK-21 cells coexpressing human secretory glycoproteins and human Gal(beta-1-4)GlcNAc-R alpha-2,6-sialyltransferase alpha-2,6-Linked NeuAc is preferentially attached to the Gal(beta-1-4)GlcNAc(beta-1-2)Man(alpha-1-3)-branch of diantennary oligosaccharides from secreted recombinant beta-trace protein, Eur. J. Biochem, 1995, pp. 718-725, vol. 232, No. 3, Berlin, Germany.
Grand et al., "Modulation of the level of expression of cellular genes in adenovirus 12-infected and transformed human cells," Eur Mol Biol Organ J. 1986, 5 (6) 1253-1260. Abstract.
Grand et al., "The high levels of p53 present in adenovirus early region 1-transformed human cells do not cause up-regulation of MDM2 expression," Virology, 1995, vol. 210, No. 2, pp. 323-334. Abstract.
Hollister et al., Stable expression of mammalian beta1,4-galactosyltransferase extends the N-glycosylation pathway in insect cells, Glycobiology, 1998, pp. 473-480, vol. 8, No. 5, IRL Press, United Kingdom.
Jenkins et al., Getting the glycosylation right: Implications for the biotechnology industry, Nature Biotechnology, Aug. 1996, pp. 975-981, vol. 14, No. 8, Nature Publishing, US.

Minch et al., Tissue Plasminogen Activator Coexpressed in Chinese Hamster Ovary Cells with alpha(2,6)-Sialyltransferase Contains NeuAc-alpha(2,6)Gal-beta(1,4)Glc-N-AcR Linkages, Biotechnol. Prog., 1995, pp. 348-351, vol. 11, No. 3.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Pau et al., Abstract, The human cell line PER.C6 provides a new manufacturing system for the production of influenza vaccines, Vaccine, Mar. 21, 2001, pp. 2716-2721, vol. 19, No. 17-19.

Pazur et al., Abstract, Oligosaccharides as immununodeterminants of erythropoietin for two sets of anti-carbohydrate antibodies, Journal of Protein Chemistry, Nov. 2000, pp. 631-635, vol. 19, No. 8.

Schiedner et al., Abstract, Efficient transformation of primary human amniocytes by E1 functions of Ad5: generation of new cell lines for adenoviral vector production, 2000, Hum. Gene Ther. 11, 2105-2116.

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Yu et al., "Enhanced c-erbB-2/neu expression in human ovarian cancer cells correlates with more severe malignancy that can be suppressed by E1A," Cancer Res., 1993, 53 (4) 891-8. Abstract.

Zhang et al., Stable expression of human alpha-2,6-sialyltransferase in Chinese hamster ovary cells: functional consequences for human erythropoietin expression and bioactivity, BBA—General Subjects, 1998, pp. 441-452, vol. 1425, No. 3, Elsevier Science Publishers, NL.

* cited by examiner

SEQUENCE LISTING

```
<160> NUMBER OF SEQ ID NOS: 8

<210> SEQ ID NO 1
<211> LENGTH: 2022
<212> TYPE: DNA
<213> ORGANISM: Artificial
<220> FEATURE:
<223> OTHER INFORMATION: Genomic DNA encoding heavy chain of anti-EpCAM
      IgA
<220> FEATURE:
<221> NAME/KEY: misc_feature
<222> LOCATION: (1)..(3)
<223> OTHER INFORMATION: Start codon
<220> FEATURE:
<221> NAME/KEY: misc_feature
```

<222> LOCATION: (2020)..(2022)
<223> OTHER INFORMATION: Stop codon

<400> SEQUENCE: 1

```
atggcatgcc ctggcttcct gtgggcactt gtgatctcca cctgtcttga attttccatg      60
gcccaggtgc agctggtgca gtctggggct gaggtgaaga agcctgggtc ctcggtgagg     120
gtctcctgca aggcttctgg aggcaccttc agcagctatg ctatcagctg ggtgcgacag     180
gcccctggac aagggcttga gtggatggga gggatcatcc ctatctttgg tacagcaaac     240
tacgcacaga gttccaggg cagagtcacg attaccgcgg acgaatccac gagcacagcc      300
tacatggagc tgagcagcct gagatctgag gacacggctg tgtattactg tgcaagagac     360
ccgtttcttc actattgggg ccaaggtacc ctggtcaccg tctcgacagg tgagtgcggc     420
cgctctgtgc tgggttcctc cagtatagag gagaggcagg cacagactgt cctcctgggg     480
acatggcatg agggccgcgt cctcacagtg cattctgtgt ccagcatcc ccgaccagcc      540
ccaaggtctt cccgctgagc ctctgcagca cccagccaga tggaacgtg gtcatcgcct      600
gcctggtcca gggcttcttc cccaggagc cactcagtgt gacctggagc gaaagcggac      660
agggcgtgac cgccagaaac ttcccaccca gccaggatgc ctccggggac ctgtacacca     720
cgagcagcca gctgaccctg ccggccacac agtgcctagc cggcaagtcc gtgacatgcc     780
acgtgaagca ctacacgaat cccagccagg atgtgactgt gccctgccca ggtcagaggg     840
caggctgggg agtggggcgg ggccaccccg tcgtgccctg acactgcgcc tgcacccgtg     900
ttccccacag ggagccgccc cttcactcac cagagtgg accgcgggcc gagccccagg      960
aggtggtggt ggacaggcca ggaggggcga ggcggggca tggggaagca tgtgctgacc    1020
agctcaggcc atctctccac tccagttccc tcaactccac ctaccccatc tccctcaact   1080
ccacctaccc catctccctc atgctgccac cccgactgt cactgcaccg accggccctc    1140
gaggacctgc tcttaggttc agaagcgaac ctcacgtgca cactgaccgg cctgagagat   1200
gcctcaggtg tcaccttcac ctggacgccc tcaagtggga agagcgctgt tcaaggacca   1260
cctgaccgtg acctctgtgg ctgctacagc gtgtccagtg tcctgtcggg ctgtgccgag   1320
ccatggaacc atgggaagac cttcacttgc actgctgcct accccgagtc caagacccg   1380
ctaaccgcca ccctctcaaa atccggtggg tccagaccct gctcggggcc ctgctcagtg   1440
ctctggtttg caaagcatat tcctggcctg cctcctccct cccaatcctg ggctccagtg   1500
ctcatgccaa gtacagaggg aaactgaggc aggctgaggg gccaggacac agcccggggt   1560
gcccaccaga gcagaggggc tctctcatcc cctgcccagc cccctgacct ggctctctac   1620
cctccaggaa acacattccg gcccgaggtc cacctgctgc cgccgccgtc ggaggagctg   1680
gccctgaacg agctggtgac gctgacgtgc ctggcacgtg gcttcagccc caaggatgtg   1740
ctggttcgct ggctgcaggg gtcacaggag ctgccccgcg agaagtacct gacttgggca   1800
tcccggcagg agcccagcca gggcaccacc accttcgctg tgaccagcat actgcgcgtg   1860
gcagccgagg actggaagaa gggggacacc ttctcctgca tggtgggcca cgaggccctg   1920
ccgctggcct tcacacagaa gaccatcgac cgcttggcgg gtaaacccac ccatgtcaat   1980
gtgtctgttg tcatggcgga ggtggacggc acctgctact ga                       2022
```

<210> SEQ ID NO 2
<211> LENGTH: 922
<212> TYPE: DNA
<213> ORGANISM: Artificial
<220> FEATURE:
<223> OTHER INFORMATION: Genomic DNA encoding light chain of anti-EpCAM

```
        IgA
<220> FEATURE:
<221> NAME/KEY: misc_feature
<222> LOCATION: (1)..(3)
<223> OTHER INFORMATION: Start Codon
<220> FEATURE:
<221> NAME/KEY: misc_feature
<222> LOCATION: (920)..(922)
<223> OTHER INFORMATION: Stop Codon

<400> SEQUENCE: 2
atggcatgcc ctggcttcct gtgggcactt gtgatctcca cctgtcttga attttccatg      60
gctgaaattg agctcactca gtctccactc tccctgcccg tcaccctgg agagccggcc     120 tccatctcct gcaggtctag tcagagcctc ctgcatagta atggatacaa ctatttggat     180
tggtacctgc agaagccagg gcagtctcca cagctcctga tctatttggg ttctaatcgg     240
gcctccgggg tccctgacag gttcagtggc agtggatcag gcacagattt tacactgaaa     300
atcagcagag tggaggctga ggatgttggg gtttattact gcatgcaagc tctacaaact     360
ttcactttcg gccctgggac caaggtggag atcaaacgta agtgcacttt gcggccgcta     420
ggaagaaact caaacatca agattttaaa tacgcttctt ggtctccttg ctataattat     480
ctgggataag catgctgttt tctgtctgtc cctaacatgc cctgtgatta ccgcaaaca     540 acacacccaa gggcagaact tgttactta aacaccatcc tgtttgcttc tttcctcagg     600
aactgtggct gcaccatctg tcttcatctt cccgccatct gatgagcagt tgaaatctgg     660
aactgcctct gttgtgtgcc tgctgaataa cttctatccc agagaggcca agtacagtg     720 gaaggtggat aacgccctcc aatcgggtaa ctcccaggag agtgtcacag agcaggacag     780
caaggacagc acctacagcc tcagcagcac cctgacgctg agcaaagcag actacgagaa     840
acacaaagtc tacgcctgcg aagtcaccca tcagggcctg agctcgcccg tcacaaagag     900
cttcaacagg ggagagtgtt ag                                              922

<210> SEQ ID NO 3
<211> LENGTH: 489
<212> TYPE: PRT
<213> ORGANISM: artificial
<220> FEATURE:
<223> OTHER INFORMATION: Amino acid sequence anti-EpCAM IgA heavy chain
<220> FEATURE:
<221> NAME/KEY: MISC_FEATURE
<222> LOCATION: (1)..(21)
<223> OTHER INFORMATION: leader peptide
<220> FEATURE:
<221> NAME/KEY: MISC_FEATURE
<222> LOCATION: (22)..(136)
<223> OTHER INFORMATION: VH Region
<220> FEATURE:
<221> NAME/KEY: MISC_FEATURE
<222> LOCATION: (137)..(238)
<223> OTHER INFORMATION: CH1 Region
<220> FEATURE:
<221> NAME/KEY: MISC_FEATURE
<222> LOCATION: (239)..(359)
<223> OTHER INFORMATION: CH2 Region
<220> FEATURE:
<221> NAME/KEY: MISC_FEATURE
<222> LOCATION: (360)..(489)
<223> OTHER INFORMATION: CH3 Region

<400> SEQUENCE: 3

Met Ala Cys Pro Gly Phe Leu Trp Ala Leu Val Ile Ser Thr Cys Leu
1               5                   10                  15

Glu Phe Ser Met Ala Gln Val Gln Leu Val Gln Ser Gly Ala Glu Val
            20                  25                  30
```

```
Lys Lys Pro Gly Ser Ser Val Arg Val Ser Cys Lys Ala Ser Gly Gly
             35                  40                  45
Thr Phe Ser Ser Tyr Ala Ile Ser Trp Val Arg Gln Ala Pro Gly Gln
         50                  55                  60
Gly Leu Glu Trp Met Gly Gly Ile Ile Pro Ile Phe Gly Thr Ala Asn
 65                  70                  75                  80
Tyr Ala Gln Lys Phe Gln Gly Arg Val Thr Ile Thr Ala Asp Glu Ser
                 85                  90                  95
Thr Ser Thr Ala Tyr Met Glu Leu Ser Ser Leu Arg Ser Glu Asp Thr
            100                 105                 110
Ala Val Tyr Tyr Cys Ala Arg Asp Pro Phe Leu His Tyr Trp Gly Gln
            115                 120                 125
Gly Thr Leu Val Thr Val Ser Thr Ala Ser Pro Thr Ser Pro Lys Val
        130                 135                 140
Phe Pro Leu Ser Leu Cys Ser Thr Gln Pro Asp Gly Asn Val Val Ile
145                 150                 155                 160
Ala Cys Leu Val Gln Gly Phe Phe Pro Gln Glu Pro Leu Ser Val Thr
                165                 170                 175
Trp Ser Glu Ser Gly Gln Gly Val Thr Ala Arg Asn Phe Pro Pro Ser
            180                 185                 190
Gln Asp Ala Ser Gly Asp Leu Tyr Thr Thr Ser Ser Gln Leu Thr Leu
        195                 200                 205
Pro Ala Thr Gln Cys Leu Ala Gly Lys Ser Val Thr Cys His Val Lys
210                 215                 220
His Tyr Thr Asn Pro Ser Gln Asp Val Thr Val Pro Cys Pro Val Pro
225                 230                 235                 240
Ser Thr Pro Pro Thr Pro Ser Pro Ser Thr Pro Pro Thr Pro Ser Pro
                245                 250                 255
Ser Cys Cys His Pro Arg Leu Ser Leu His Arg Pro Ala Leu Glu Asp
            260                 265                 270
Leu Leu Leu Gly Ser Glu Ala Asn Leu Thr Cys Thr Leu Thr Gly Leu
        275                 280                 285
Arg Asp Ala Ser Gly Val Thr Phe Thr Trp Thr Pro Ser Ser Gly Lys
290                 295                 300
Ser Ala Val Gln Gly Pro Pro Asp Arg Asp Leu Cys Gly Cys Tyr Ser
305                 310                 315                 320
Val Ser Ser Val Leu Ser Gly Cys Ala Glu Pro Trp Asn His Gly Lys
                325                 330                 335
Thr Phe Thr Cys Thr Ala Ala Tyr Pro Glu Ser Lys Thr Pro Leu Thr
            340                 345                 350
Ala Thr Leu Ser Lys Ser Gly Asn Thr Phe Arg Pro Glu Val His Leu
        355                 360                 365
Leu Pro Pro Pro Ser Glu Glu Leu Ala Leu Asn Glu Leu Val Thr Leu
370                 375                 380
Thr Cys Leu Ala Arg Gly Phe Ser Pro Lys Asp Val Leu Val Arg Trp
385                 390                 395                 400
Leu Gln Gly Ser Gln Glu Leu Pro Arg Glu Lys Tyr Leu Thr Trp Ala
                405                 410                 415
Ser Arg Gln Glu Pro Ser Gln Gly Thr Thr Thr Phe Ala Val Thr Ser
            420                 425                 430
Ile Leu Arg Val Ala Ala Glu Asp Trp Lys Lys Gly Asp Thr Phe Ser
        435                 440                 445
Cys Met Val Gly His Glu Ala Leu Pro Leu Ala Phe Thr Gln Lys Thr
450                 455                 460
```

```
Ile Asp Arg Leu Ala Gly Lys Pro Thr His Val Asn Val Ser Val Val
465                 470                 475                 480

Met Ala Glu Val Asp Gly Thr Cys Tyr
                485

<210> SEQ ID NO 4
<211> LENGTH: 239
<212> TYPE: PRT
<213> ORGANISM: Artificial
<220> FEATURE:
<223> OTHER INFORMATION: amino acid sequence anti-EpCAM IgA light chain
<220> FEATURE:
<221> NAME/KEY: MISC_FEATURE
<222> LOCATION: (1)..(21)
<223> OTHER INFORMATION: leader peptide
<220> FEATURE:
<221> NAME/KEY: MISC_FEATURE
<222> LOCATION: (22)..(132)
<223> OTHER INFORMATION: VL region
<220> FEATURE:
<221> NAME/KEY: MISC_FEATURE
<222> LOCATION: (133)..(239)
<223> OTHER INFORMATION: CL region

<400> SEQUENCE: 4

Met Ala Cys Pro Gly Phe Leu Trp Ala Leu Val Ile Ser Thr Cys Leu
1               5                   10                  15

Glu Phe Ser Met Ala Glu Ile Glu Leu Thr Gln Ser Pro Leu Ser Leu
                20                  25                  30

Pro Val Thr Pro Gly Glu Pro Ala Ser Ile Ser Cys Arg Ser Ser Gln
                35                  40                  45

Ser Leu Leu His Ser Asn Gly Tyr Asn Tyr Leu Asp Trp Tyr Leu Gln
50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
                100                 105                 110

Tyr Cys Met Gln Ala Leu Gln Thr Phe Thr Phe Gly Pro Gly Thr Lys
                115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
                195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 5
<211> LENGTH: 38
<212> TYPE: DNA
<213> ORGANISM: Artificial
<220> FEATURE:
```

```
<223> OTHER INFORMATION: E001 forward primer for amplification of light
      chain

<400> SEQUENCE: 5
cctggcgcgc caccatggca tgccctggct tcctgtgg                              38

<210> SEQ ID NO 6
<211> LENGTH: 32
<212> TYPE: DNA
<213> ORGANISM: Artificial
<220> FEATURE:
<223> OTHER INFORMATION: E002 reverse primer for amplification of light
      chain

<400> SEQUENCE: 6
ccgggttaac taacactctc ccctgttgaa gc                                    32

<210> SEQ ID NO 7
<211> LENGTH: 39
<212> TYPE: DNA
<213> ORGANISM: Artificial
<220> FEATURE:
<223> OTHER INFORMATION: E003 forward primer for amplification of heavy
      chain

<400> SEQUENCE: 7
ggaggatccg ccaccatggc atgccctggc ttcctgtgg                             39

<210> SEQ ID NO 8
<211> LENGTH: 29
<212> TYPE: DNA
<213> ORGANISM: Artificial
<220> FEATURE:
<223> OTHER INFORMATION: P01 reverse primer for amplification of heavy
      chain

<400> SEQUENCE: 8
ggaccgctag ctcagtagca ggtgccgac                                        29
```

EFFICIENT PRODUCTION OF IGA IN RECOMBINANT MAMMALIAN CELLS

CROSS-REFERENCE TO RELATED APPLICATIONS

This application is a continuation-in-part of U.S. patent application Ser. No. 09/549,463, filed Apr. 14, 2000, now U.S. Pat. No. 6,855,544 B1, the contents of the entirety of which is incorporated herein by this reference, which U.S. application Ser. No. 09/549,463 claims the benefit under 35 U.S.C. §119(e) to U.S. Provisional Patent Application Ser. No. 60/129,452, filed Apr. 15, 1999. The instant application is also a continuation-in-part of co-pending PCT International Patent Application No. PCT/EP2003/007690, filed on Jul. 15, 2003, designating the United States of America, and published, in English, as International Publication No. WO 2004/009618A2 on Jan. 29, 2004, which International Patent Application claims the benefit under 35 U.S.C. §119(e) to U.S. Provisional Application No. 60/397,066, filed Jul. 18, 2002. The instant application is also a continuation-in-part of co-pending International Patent Application No. PCT/EP03/50201, filed May 27, 2003, designating the United States of America.

TECHNICAL FIELD

The invention relates to the field of recombinant protein production. More particularly, the invention relates to the production of immunoglobulins of class A (IgA) in recombinant mammalian host cells.

BACKGROUND

Immunoglobulin molecules may be one of five classes based on amino acid sequence of the constant region of the molecule. These classes are IgG, IgM, IgA, IgD and IgE. Each class has different biological roles based on class-specific properties (Roitt, I., Brostoff, J., Make, D. (2001), *Immunology*, 6$^{th}$ edition, pub. Mosby).

IgA is the first line of immune defense on mucosal surfaces where it is produced at approximately 3-5 g/day. Furthermore it is present in serum at around 3 mg/ml, and as such is the most abundantly produced immunoglobulin. One IgA monomer comprises two heavy chains and two light chains. Light chains may be of the kappa or lambda class, and are shared with other immunoglobulin classes. The heavy chains of IgA consist of an N-terminal variable region, followed by a constant region, a hinge region, and then two additional constant regions. At the C-terminus there is a tail-piece which has a function in dimerization of the molecule. IgA is found as two different isoforms, IgA1 and IgA2; the main difference in these isotypes is found in the hinge region, where IgA2 lacks a proline-rich region which in IgA1 is susceptible to bacterial protease activity. IgA1 is the predominant isotype in serum, whereas IgA2 is mainly produced by cells of the lamina propria where it is secreted on to mucosal surfaces. IgA2 is further divided into IgA(m)1 and IgA(m)2, depending on the nature of the disulphide linkage of heavy and light chains (Chintalacharuvu and Morrison, 1999).

Plasma IgA is found predominantly as a monomeric species, but mucosal IgA exists primarily in a dimeric form. A 15 kDa J-chain binds to the molecule, stabilizing the dimeric form, and upon secretion to the mucosal surface a 50-90 kDa secretory component becomes complexed to the molecule. This protects the IgA from degradation on the luminal surface (Johansen et al., 2000, 2001).

The IgA1 hinge region includes three to five O-linked glycans, and the heavy chain includes two N-linked glycans (Mattu et al., 1998; Novak et al., 2000). The IgA2 subclass contains an additional two or three N-linked glycans. The role these glycans play in protein stability or effector function is not clear.

IgG1 does not bind neutrophils with a high affinity, and therefore is not proficient in neutrophil activation. IgA exerts its biological effects by a variety of mechanisms (Dechant and Valerius, 2001). It binds to the FcαRI receptor (CD89), which is expressed on neutrophils, eosinophils, monocytes/macrophages, though not on NK cells. Activation of FcαRI causes responses such as the oxidative burst and degranulation, but is also important in the triggering of phagocytosis. Neutrophils are the most prevalent lymphocytes in the blood and when activated are a powerful tool to combat infection. A second mechanism by which IgA exerts a response is by directly binding to and neutralizing pathogens at mucosal surfaces, an effect enhanced by the dimeric nature of the IgA. Additionally, a mechanism by which antibodies are thought to eliminate target cells is by binding to, and often cross-linking, cell surface receptors (Ghetie et al., 1997; Tutt et al., 1998; Longo, 2002). This can lead to activation of signaling pathways resulting in arrest of cell growth or apoptosis. IgA does not appear to activate complement, but the other effector functions make it a potentially valuable adjunct to IgG in the clinical treatment of disease.

Few studies have been performed to test the value of IgAs as therapeutics (reviewed in Dechant and Valerius, 2001; Corthesy, 2002), in part because murine IgA does not bind the human FcαRI. Some studies have been performed which demonstrate IgA activity against infectious disease (Vidarsson et al., 2001; Spriel et al., 1999), and a few studies to look at cancer immunotherapy (Huls et al., 1999a; van Egmond et al., 2001).

There is also little data in the literature regarding IgA production in cell lines (reviewed in Chintalacharuvu and Morrison, 1999; Yoo et al., 2002). There is little information regarding productivity of such cells, but IgA production of up to 20 pg per cell per 24 hours has been described in Chinese Hamster Ovary (CHO) cells, though this included gene amplification (Berdoz et al., 1999). However, cells with high copy numbers of the transgene are reported to display instability upon propagation of the cells (Kim et al., 1998; Barnes et al., 2003). Glycan structures present on an IgA molecule produced in CHO cells has also been analyzed, and it was found that CHO cells produced predominantly tri-antennary structures, whereas serum IgA contains mostly bi-antennary structures (Mattu et al., 1998). This may reflect a difference between human cells and CHO cell culture.

A need remains for a good production platform for recombinant IgA production, without the drawbacks associated with the existing platforms.

DISCLOSURE OF THE INVENTION

The characteristics of a platform for production of IgA preferably include high IgA productivity and human-type glycosylation of the molecule. It is demonstrated herein that PER.C6™ cells (Crucell NV of Leiden, NL) are capable of efficiently producing and secreting recombinant IgA molecules. High levels of IgA are expressed from recombinant cells without the need for amplification of the copy number of the recombinant nucleic acid encoding the IgA.

In one aspect, the invention provides a cell expressing E1A and E1B proteins of an adenovirus, wherein the cell includes recombinant nucleic acid encoding an IgA molecule in expressible format.

In another aspect, the invention provides a method for recombinant production of an IgA molecule, the method including: a) providing a cell expressing E1A and E1B proteins of an adenovirus, wherein the cell further includes recombinant nucleic acid encoding an IgA molecule in expressible format; and b) culturing the cell and expressing the recombinant nucleic acid encoding an IgA. In another aspect, the invention provides for the use of a cell expressing E1A and E1B proteins of an adenovirus for recombinant expression of IgA molecules. In certain embodiments, the cells are derived from retina cells. In other embodiments, the cells are derived from primary cells, which have been immortalized by the expression of E1A and E1B proteins. In other embodiments, the cells are human cells. In preferred embodiments, the cells of the invention are immortalized human retina cells, more preferably, PER.C6™ cells, or cells derived therefrom.

BEST MODE OF THE INVENTION

We have found that cells derived from human retina cells, which have been immortalized by introduction of E1 sequences from an adenovirus, are a good production platform for recombinant IgA molecules. A method for immortalization of embryonic retina cells has been described in U.S. Pat. No. 5,994,128, the contents of which are incorporated by this reference. Accordingly, an embryonic retina cell that has been immortalized with E1 sequences from an adenovirus can be obtained by that method. Other cells expressing E1A and E1B of an adenovirus can be prepared accordingly. Preferably, the cells of the invention are human cells. In certain embodiments, the cells are derived from retina cells. Preferably the cells are derived from primary cells. A cell according to the invention expresses at least the E1A region of an adenovirus, and preferably also the E1B region. E1A protein has transforming activity, while E1B protein has anti-apoptotic activities. The cells of the invention therefore preferably express E1A and E1B proteins of an adenovirus. In preferred embodiments, such cells are derived from PER.C6™ cells (human embryonic retinoblast cell line containing in its genome human adenovirus type 5 (Ad5) E1A and E1B coding sequences (nt. 459-3510) under the control of the human phosphoglycerate kinase (PGK) promoter), as deposited under ECACC number 96022940 on Feb. 29, 1996 at the Centre for Applied Microbiology and Research Authority (European Collection of Animal Cell Cultures), Porton Down, Salisbury, Wiltshire SP4, OJG, United Kingdom, an International Depository Authority. Cells derived from a PER.C6™ cell according to the invention can be obtained by introduction of foreign genetic material encoding an IgA molecule into such PER.C6™ cells. Preferably, the cells are from a stable clone that can be selected and propagated according to standard procedures known to the person skilled in the art. A culture of such a clone is capable of producing recombinant IgA molecules. Cells according to the invention are preferably able to grow in suspension culture in serum-free medium.

It has previously been shown that PER.C6™ cells can express intact human IgG (U.S. Patent Application Serial No. 2003-0092160-A1, the contents of which is incorporated by this reference), that such IgGs have human-type glycans and the cells can be grown at large scale (Jones et al., 2003; Nichols et al., 2002). We have found that these cells can efficiently produce an additional class of immunoglobulins having different characteristics. It was unexpectedly found that IgA can be produced in PER.C6™ cells at levels comparable to those for IgG.

To obtain expression of nucleic acid sequences encoding IgA, it is well known to those skilled in the art that sequences capable of driving such expression can be functionally linked to the nucleic acid sequences encoding the IgA molecules, resulting in recombinant nucleic acid molecules encoding an IgA in expressible format. "Functionally linked" is meant to describe that the nucleic acid sequences encoding the IgA antibody fragments or precursors thereof are linked to the sequences capable of driving expression such that these sequences can drive expression of the antibodies or precursors thereof.

Useful expression vectors are available in the art, e.g., the pcDNA vector series of Invitrogen. Where the sequence encoding the IgA polypeptide of interest is properly inserted with reference to sequences governing the transcription and translation of the encoded polypeptide, the resulting expression cassette is useful to produce the IgA of interest, referred to as expression. Sequences driving expression may include promoters, enhancers and the like, and combinations thereof. These should be capable of functioning in the host cell, thereby driving expression of the nucleic acid sequences that are functionally linked to them.

Promoters can be constitutive or regulated, and can be obtained from various sources, including viruses, prokaryotic, or eukaryotic sources, or artificially designed.

Expression of nucleic acids of interest may be from the natural promoter or derivative thereof or from an entirely heterologous promoter. Some well-known and much used promoters for expression in eukaryotic cells include promoters derived from viruses, such as adenovirus, e.g., the E1A promoter, promoters derived from cytomegalovirus (CMV), such as the CMV immediate early (IE) promoter, promoters derived from Simian Virus 40 (SV40), and the like. Suitable promoters can also be derived from eukaryotic cells, such as methallothionein (MT) promoters, elongation factor 1α (EF-1α) promoter, actin promoter, an immunoglobulin promoter, heat shock promoters, and the like. In one embodiment the sequence capable of driving expression includes a region from a CMV promoter, preferably the region including nucleotides −735 to +95 of the CMV immediate early gene enhancer/promoter. This gives particularly high expression levels in cells expressing E1A of an adenovirus.

Culturing a cell is done to enable it to metabolize, and/or grow and/or divide and/or produce recombinant proteins of interest. Such culturing can be accomplished by methods well known to persons skilled in the art, and includes but is not limited to providing nutrients for the cell. The methods include growth by adherence to surfaces, growth in suspension, or combinations thereof. Several culturing conditions can be optimized by methods well known in the art to optimize protein production yields. Culturing can be done for instance in dishes, roller bottles or in bioreactors, using batch, fed-batch, continuous systems, hollow fiber, and the like. In order to achieve large scale (continuous) production of recombinant proteins through cell culture it is preferred in the art to have cells capable of growing in suspension, and it is preferred to have cells capable of being cultured in the absence of animal- or human-derived serum or animal- or human-derived serum components. Thus, purification is easier and safety is enhanced due to the absence of additional animal or human proteins derived from the culture medium, while the system is also very reliable as synthetic media are the best in reproducibility.

The conditions for growing or multiplying cells (see e.g., *Tissue Culture*, Academic Press, Kruse and Paterson, editors (1973)) and the conditions for expression of the recombinant product may differ somewhat, and optimization of the process is usually performed to increase the product yields and/or growth of the cells with respect to each other, according to methods generally known to the person skilled in the art. In general, principles, protocols, and practical techniques for maximizing the productivity of mammalian cell cultures can be found in *Mammalian Cell Biotechnology: a Practical Approach* (M. Butler, ed., IRL Press, 1991).

The IgA is expressed in the cells according to the invention, and may be recovered from the cells or preferably from the cell culture medium, by methods generally known to persons skilled in the art. Such methods may include precipitation, centrifugation, filtration, size-exclusion chromatography, affinity chromatography, cation- and/or anion-exchange chromatography, hydrophobic interaction chromatography, and the like.

It is demonstrated herein that IgA can be expressed at high levels without the necessity for first amplifying the nucleic acid sequences encoding the IgA within the host cells. This has the advantage that no large copy numbers are required for efficient expression according to the invention, in contrast to previously described recombinant IgA production systems, where amplification was required to obtain levels of around 20 pg IgA per cell per day. Preferably, the cells, when seeded at $0.5\times10^6$ cells/well and cultured in 6-well tissue culture plates at 37° C. in DMEM with 10% serum under an atmosphere containing 10% $CO2$, produce at least 5 pg IgA/seeded cell/day, more preferably at least 20 pg IgA/seeded cell/day, and even more preferably, at least 40 pg IgA/seeded cell/day. PER.C6® cells expressing IgG at high levels have been shown to contain usually between one and ten copies of the nucleic acid encoding the IgG per cell (Jones et al., 2003).

Methods of determining copy numbers are known to the person skilled in the art of molecular biology, and include Southern blotting, quantitative PCR, fiber-FISH, and the like. Hence, the invention provides for a method according to the invention wherein the cells include between one and twenty, usually between one and ten copies per cell of the recombinant nucleic acid encoding the IgA molecule. This has the advantage of fast expression, as no labor-intensive and time consuming amplification step is needed to obtain clones with sufficiently high expression levels for analysis. Moreover, such cells are expected to be more stable than cells containing high copy numbers of the transgene, that are reported to display instability upon propagation of the cells (Kim et al., 1998; Barnes et al., 2003). Therefore, also in view of regulatory requirements, the cells and methods of the invention are an improvement over those of the prior art. Preferably, cells in the method of the invention express at least 5 pg IgA per seeded cell per day, more preferably at least 20 pg per seeded cell per day, still more preferably ate least 40 pg per seeded cell per day, and still more preferably at least 50 pg per seeded cell per day. Levels up to 60 pg per seeded cell per day are herein reported.

The IgA production system of the invention is not dependent upon co-expression of the J-chain for production of functional IgA. Optionally however, J-chain may be co-expressed.

An IgA molecule is an immunoglobulin wherein the heavy chains are alpha chains. An IgA molecule can have a monomeric or dimeric structure. An IgA molecule according to the invention may be of any origin, including human, rodent, chimeric, humanized, and the like, however human IgAs are preferred. Using a human cell line for production provides these molecules with a human-type glycosylation, resulting in production of IgA molecules that are not recognized as foreign by the human immune system, because both the polypeptide and the glycan portion are human. The person skilled in the art will be aware of the possibilities to obtain human IgA sequences. The sequences for the constant regions are known, and are also provided herein. Sequences encoding human variable regions may, for example, be obtained by known methods such as phage display (methods, e.g., described in CF Barbas III et al., *Phage Display, A laboratory manual*, Cold Spring Harbor Laboratory Press, Cold Spring Harbor, N.Y., 2001) or by immunizing transgenic mice that include genetic material encoding a human immunoglobulin repertoire (Fishwild et al., 1996; Mendez et al., 1997).

Antibodies may be used as naked molecules, or they may be in the form of immunoconjugates or labeled molecules, and so used as a magic bullet to deliver a cargo to a tumor or infection for therapy or imaging (Carter, 2001; Borrebaeck and Carlsson, 2001; Park and Smolen, 2001). Immunoconjugates include antigen binding domains and a non-antibody part such as a toxin, a radiolabel, an enzyme, and the like. IgA molecules may be labeled in the same way as IgG molecules. Hence, the term IgA molecule as used herein includes naked IgA molecules, but may also refer to immunoconjugates including IgA molecules.

The IgA generated in this study is against the human tumor antigen EpCAM (epithelial cell adhesion molecule), a 40 kDa glycoprotein expressed on the surface of colon carcinoma cells. The high expression of EpCAM on colon carcinomas makes it an attractive target for immunotherapy. The antibody was isolated from a semi-synthetic phage library as a single chain Fv fragment named UBS54 (WO 01/48485; Huls et al., 1999b). In one aspect the invention therefore provides a recombinant human IgA molecule that is capable of binding to EpCAM. In other embodiments, human IgA molecules are used for the preparation of a medicament and/or for direct treatment of a disease such as cancer.

EXAMPLES

The invention will now be described by some illustrative examples. In practice, the invention generally employs, unless otherwise indicated, conventional techniques of immunology, molecular biology, microbiology, microbiology, cell biology, and recombinant DNA, which are within the skill of the art. See, e.g., Sambrook, J. and Russell, D. W. (2001), *Molecular cloning: a laboratory manual*, Pub. Cold Spring Harbor Laboratory Press; *Current Protocols in Molecular Biology*, Ausubel F. M., et al., eds, 1987; the series *Methods in Enzymology* (Academic Press, Inc.); *PCR2: A Practical Approach*, MacPherson M. J., Hams B. D., Taylor G. R., eds, 1995; *Antibodies: A Laboratory Manual*, Harlow and Lane, eds, 1988.

Example I

Construction of pEpcamIgA Expression Vector

An expression plasmid was generated which encodes both the light and heavy chains of an IgA antibody that recognizes EpCAM. The DNA encoding the antigen-binding region of this antibody was first isolated from a scFv phage display library (Huls et al., 1999). A leader sequence and constant regions were added essentially as described in Boel et al., 2000. The genomic DNA encoding the light and heavy chains (genomic sequences of the antibody-encoding regions provided in SEQ ID NO:1 and SEQ ID NO:2, amino acid sequences of the encoded anti-EpCAM IgA provided in SEQ ID NO:3 and SEQ ID NO:4) were then amplified using PCR to append convenient restriction sites, and then cloned into the expression vector pcDNA3002(Neo). The following primers were used for PCR of the light chain:

```
                                         (SEQ ID NO: 5)
E001: CCTGGCGCGCCACCATGGCATGCCCTGGCTTCCTGTGG (SEQ ID NO: 6)
E002: CCGGGTTAACTAACACTCTCCCCTGTTGAAGC.
```

The following primers were used for PCR of the heavy chain:

```
                                         (SEQ ID NO: 7)
E003: GGAGGATCCGCCACCATGGCATGCCCTGGCTTCCTGTGG (SEQ ID NO: 8)
P01: GGACCGCTAGCTCAGTAGCAGGTGCCGAC.
```

Figure 1:
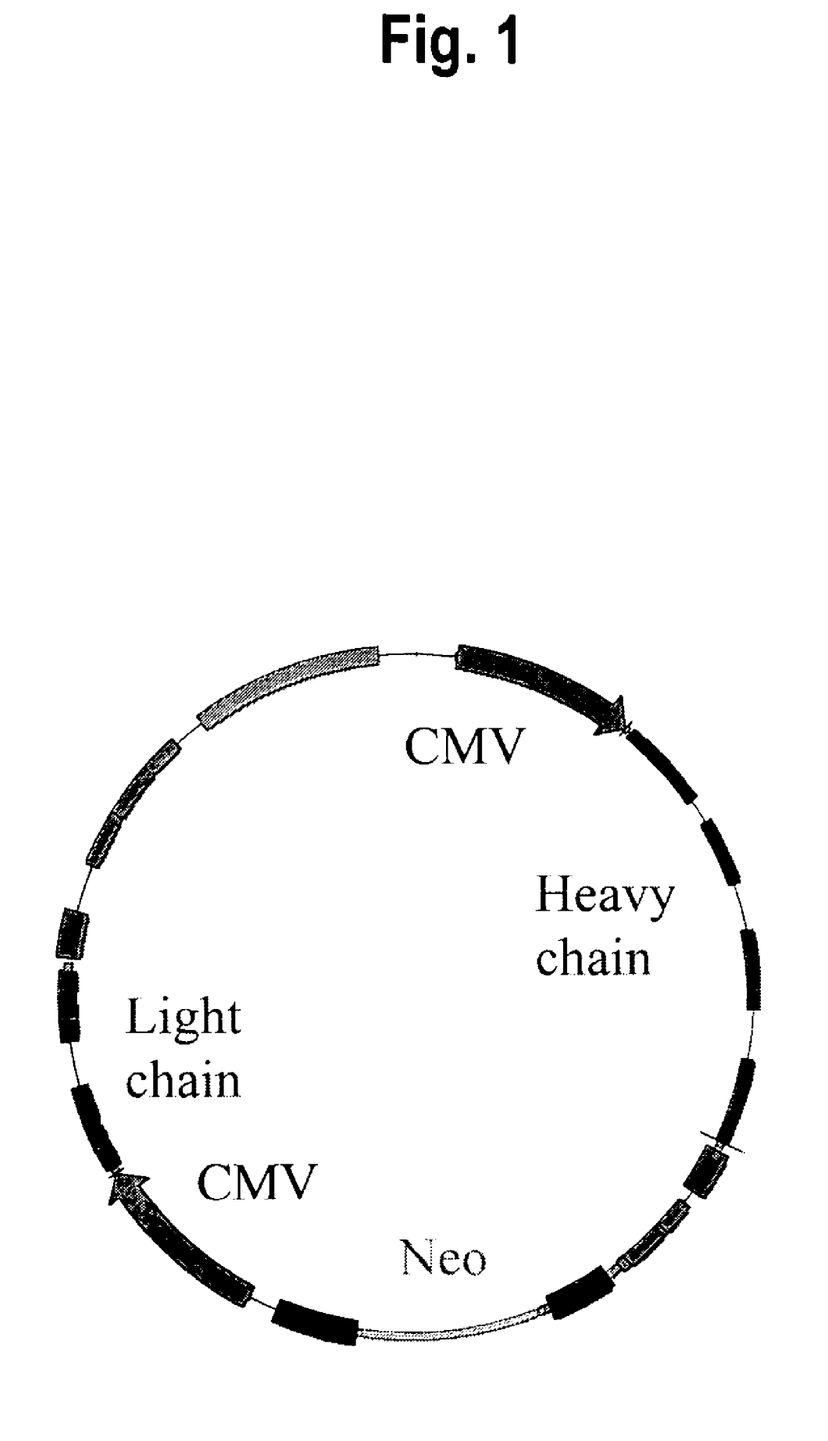
FIG. 1. Vector for expression of intact IgA. IgA-encoding regions, CMV promoters and the neomycin resistance marker are indicated.

The start codon (E001, E003) and stop codon (E002, P01) are in bold. Restriction sites AscI (E001), HpaI (E002), BamHI (E003) and NheI (P01) are underlined. Primers E001 and E003 also include a Kozak sequence (italics). The light chain fragment of approximately 0.9 kb was digested with AscI-HpaI and inserted into pcDNA3002(Neo) digested with the same enzymes. The heavy chain fragment of approximately 2.0 kb was then digested with BamHI-NheI and inserted into pcDNA3002(Neo) containing the light chain digested with the same enzymes. The resulting plasmid is pEpcamIgA (FIG. 1). The generated construct contains DNA encoding a kappa light chain and an alpha1 heavy chain, both preceded by a CMV promoter. The expression vector pcDNA3002(Neo), which has been described in international patent application PCT/NL02/00841, was deposited on Dec. 13, 2001 at the European Collection of Cell Cultures (ECACC) under number 01121318.

Example II

Transfection of PER.C6™ Cell Line and Production of IgA

Cells were transfected with pEpcamIgA by a Lipofectamine based method. In brief, PER.C6™ cells were seeded at $3.5 \times 10^6$ cells per 96 mm tissue culture dish. For each dish, 2 µg plasmid DNA was mixed with 10 µl Lipofectamine (Gibco); this was added to the cells in serum free DMEM medium (total volume 7 ml) and incubated for four hours. This was then replaced with DMEM medium (i.e., containing serum). The following day (and for the ensuing three weeks) cells were grown in DMEM medium in the presence of 0.5 mg/ml Geneticin (G418) to select for clones that were stably transfected with the plasmid. Clones were tested for IgA productivity by ELISA analysis. In brief, cells were plated at $0.5 \times 10^6$ cells per well of a 6-well dish in DMEM serum. These were incubated for four days, after which time supernatant was harvested and IgA concentration measured. For ELISA analysis, wells of a 96-well plate were coated with antibody raised against Ig kappa light chain. After blocking with a BSA solution, samples were added to wells at varying dilutions and incubated for one hour. The standard used was human IgA (Accurate Chemical cat. YSRT-PHP002). After washing, detection antibody (HRP-labelled anti-IgA) was applied for 30 minutes. After a further washing step, substrate O-phenylene diamine dihydrochloride was added. Antibody concentration was determined by comparing optical density at 492 nm with that of the known antibody standard. The highest-producing clones produced around 60 pg IgA/seeded cell/day. This is comparable to results seen when IgG-producing cell lines are measured with the same analysis.

Figure 2:
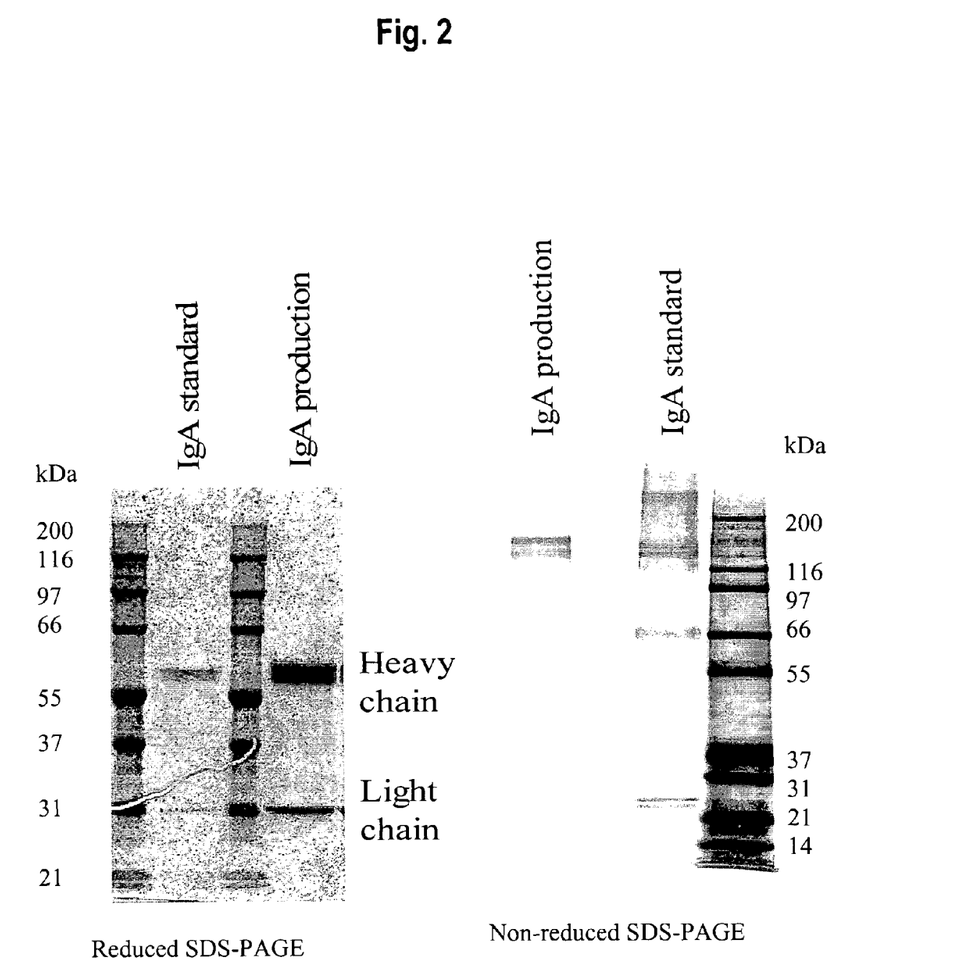
FIG. 2. Reducing and non-reducing SDS-PAGE (silver-stained) of crude cell culture supernatant from a clone producing IgA. An IgA standard is also included.

Production of antibody was performed in, serum-free medium. Thus the adherent cells in tissue culture flasks were transferred to roller bottles in PER.C6™ suspension growth medium (under which conditions the cells grow in suspension). After one week, supernatant was harvested and electrophoresed on reducing and non-reducing SDS-PAGE (FIG. 2). The reducing gel indicates that IgA is produced efficiently, with essentially all protein either intact light or intact heavy chain. The heavy chains of both the anti-Epcam sample and the standard IgA run as a doublet; the reason for this is unclear. The non-reducing gel shows that the IgA has a molecular weight of between 116 and 200 kDa; this shows that the species produced is monomeric, and no evidence of high molecular weight aggregated material or low molecular weight fragments are visible. Again the protein runs as a doublet; the control material is also present as a doublet, but also contains many unidentified bands.

The examples above demonstrate that PER.C6™ cells may be transfected with a plasmid expressing IgA to give cells with a high IgA productivity.

REFERENCES

Barnes, L. M., Bentley, C. M., Dickson, A. J. (2003). Stability of protein production from recombinant mammalian cells. Biotechnol. and Bioeng. 81, 631-639.

Berdoz, J., Blanc, C. T., Reinhardt, M., Kraehenbuhl, J., Corthesy, B. (1999). In vitro comparison of the antigen-binding and stability properties of the various molecular forms of IgA antibodies assembled and produced in CHO cells. Proc. Natl. Acad. Sci. USA. 96, 3029-34.

Boel, E., Verlaan, S., Poppelier, M. J., Westerdaal, N. A., Van Strijp, J. A., Logtenberg, T. (2000). Functional human monoclonal antibodies of all isotypes constructed from phage display library-derived single-chain Fv antibody fragments. J. Immunol. Methods. 239, 153-66.

Borrebaeck, C. A. K. and Carlsson, R. (2001). Human therapeutic antibodies. Curr. Op. Pharmacol. 1, 404-408.

Carter, P. (2001). Improving the efficacy of antibody-based cancer therapies. Nature Reviews: Cancer 1, 118-129.

Chintalacharuvu, K. R., Morrison, S. L. (1999). Production and characterization of recombinant IgA. Immunotechnol. 4, 165-174.

Corthesy, B. (2002). Recombinant immunoglobulin A: powerful tools for fundamental and applied research. Trends in Biotechnol. 20, 65-71.

Dechant, M. and Valerius, T. (2001). IgA antibodies for cancer therapy. Crit. Rev. in Oncol./Haematol. 39, 69-77.

van Egmond, M., van Spriel, A. B., Vermeulen, H., Huls, G., van Garderen, E., van de Winkel, J. G. (2001). Enhancement of polymorphonuclear cell-mediated tumor cell killing on simultaneous engagement of fcgammaRI (CD64) and fcalphaRI (CD89). Cancer Res. 61, 4055-4060.

Fishwild, D. M., O'Donnell, S. L., Bengoechea, T., Hudson, D. V., Harding, F., Bernhard, S. L., Jones, D., Kay, R. M., Higgins, K. M., Schramm, S. R., Lonberg, N. (1996). High-avidity human IgG kappa monoclonal antibodies from a novel strain of minilocus transgenic mice. Nat. Biotechnol. 14, 845-51. Cancer Immunol. Immunother. 30, 43-50.

Ghetie, M. A., Podar, E. M., Ilgen, A., Gordon, B. E., Uhr, J. W., Vitetta, E. S. (1997). Homodimerization of tumor-reactive monoclonal antibodies markedly increases their ability to induce growth arrest or apoptosis of tumor cells. Proc. Natl. Acad. Sci. USA. 94, 7509-14.

Huls, G., Heijnen, I. A., Cuomo, E., van der Linden, J., Boel, E., van de Winkel, J. G., Logtenberg, T. (1999a). Antitumor immune effector mechanisms recruited by phage display-derived fully human IgG1 and IgA1 monoclonal antibodies. Cancer Res. 59, 5778-5784.

Huls, G. A., Heijnen, I. A. F. M., Cuomo, M. E., Koningsberger, J. C., Wiegman, L., Boel, E., van der Vuurst-de Vries, A-R., Loyson, S. A. J., Helfrich, W., van Berge Henegouwen, G. P., van Meijer, M., de Kruif, J., Logtenberg, T. (1999b). A recombinant, fully human monoclonal antibody with antitumor activity constructed from phage-displayed antibody fragments. Nat. Biotechnol. 17, 276-281.

Johansen F. E., Braathen R., Brandtzaeg P. (2000). Role of J chain in secretory immunoglobulin formation. Scand. J. Immunol. 52, 240-248.

Johansen, F. E., Braathen, R., Brandtzaeg, P. (2001). The J chain is essential for polymeric Ig receptor-mediated epithelial transport of IgA. J. Immunol. 167, 5185-5192.

Jones, D., Kroos, N., Anema, R., Van Montfort, B., Vooys, A., Van Der Kraats, S., Van Der Helm, E., Smits, S., Schouten, J., Brouwer, K., Lagerwerf, F., Van Berkel, P., Opstelten, D-J., Logtenberg, T., Bout, A. (2003). High-level expression of recombinant IgG in the human cell line PER.C6™. Biotechnol. Prog. 19, 163-8.

Kim, S. J., Kim, N. S., Ryu, C. J., Hong, H. J., Lee, G. M. (1998). Characterization of chimeric antibody producing CHO cells in the course of dihydrofolate reductase-mediated gene amplification and their stability in the absence of selective pressure. Biotechnol. Bioeng. 58, 73-84.

Longo, D. L. (2002). DR's orders: human antibody kills tumors by direct signalling. Nat. Med. 8, 781-783.

Mattu, T. S., Pleass, R. J., Willis, A. C., Kilian, M., Wormald, M. R., Lellouch, A. C., Rudd, P. M., Woof, J. M., Dwek, R. A. (1998). The glycosylation and structure of human serum IgA1, Fab, and Fc regions and the role of N-glycosylation on Fc alpha receptor interactions. J. Biol. Chem. 273, 2260-72.

Mendez, M. J., Green, L. L., Corvalan, J. R., Jia, X. C., Maynard-Currie, C. E., Yang, X. D., Gallo, M. L., Louie, D. M., Lee, D. V., Erickson, K. L., Luna, J., Roy, C. M., Abderrahim, H., Kirschenbaum, F., Noguchi, M., Smith, D. H., Fukushima, A., Hales, J. F., Klapholz, S., Finer, M. H., Davis, C. G., Zsebo, K. M., Jakobovits, A. (1997). Functional transplant of megabase human immunoglobulin loci recapitulates human antibody response in mice. Nat. Genet. 15, 146-56.

Nichols, W. W., Lardenoije, R., Ledwith, B. J., Brouwer, K., Manam, S., Vogels, R., Kaslow, D., Zuidgeest, D., Bett, A. J., Chen, L., van der Kaaden, M., Galloway, S. M., Hill, R. B., Machotka, S. V., Anderson, C. A., Lewis, J., Martinez, D., Lebron, J., Russo, C., Valerio, D. and Bout, A. (2002). Propagation of adenoviral vectors: use of PER.C6 cells. In *Adenoviral vectors for gene therapy*, (Ed. Curiel D. T. and Douglas, J. T.). Pub. Academic Press.

Novak, J., Tomana, M., Kilian, M., Coward, L., Kulhavy, R., Barnes, S., Mestecky, J. (2000). Heterogeneity of O-glycosylation in the hinge region of human IgA1. Mol Immunol. 37, 1047-56.

Park, J. W. and Smolen, J. (2001). Monoclonal antibody therapy. Adv. Prot. Chem. 56, 369-421.

van Spriel, A. B., van den Herik-Oudijk, I. E., van Sorge, N. M., Vile, H. A., van Strijp, J. A., van de Winkel, J. G. (1999). Effective phagocytosis and killing of *Candida albicans* via targeting FcgammaRI (CD64) or FcalphaRI (CD89) on neutrophils. J. Infect. Dis. 179, 661-669.

Tutt, A. L., French, R. R., Illidge, T. M., Honeychurch, J., McBride, H. M., Penfold, C. A., Fearon, D. T., Parkhouse, R. M. E., Klaus, G. G. B. and Glennie, M. J. (1998). Monoclonal antibody therapy of B cell lymphoma: signalling activity on tumour cells appears more important than recruitment of effectors. J. Immunol. 161, 3176-3185.

Vidarsson, G., van der Pol, W. L., van den Elsen, J. M., Vile, H., Jansen, M., Duijs, J., Morton, H. C., Boel, E., Daha, M. R., Corthesy, B., van de Winkel, J. G. (2001). Activity of human IgG and IgA subclasses in immune defense against Neisseria meningitidis serogroup B. J. Immunol. 166, 6250-6256.

Yoo, E. M., Chintalacharuvu, K. R., Penichet, M. L., Morrison, S. L. (2002). Myeloma expression systems. J. Immunol. Meths. 261, 1-20.

What is claimed is:

1. A cell expressing E1A and E1B proteins of an adenovirus, said cell comprising a selectable marker, said recombinant nucleic acid further comprising recombinant nucleic acid encoding an IgA molecule in expressible format, wherein said cell is derived from a human embryonic retinoblast cell as deposited under ECACC number 96022940 by stable transfection of said human embryonic retinoblast cell with the recombinant nucleic acid encoding the IgA molecule in expressible format, and wherein said IgA molecule has a constant region comprising amino acids 137 to 489 of SEQ ID NO:3, wherein stable transfection may be determined by selecting those transfected human embryonic retinoblast cells capable of surviving growth in a media selective for the presence of the selectable marker.

* * * * *